(12) United States Patent
Sherry

(10) Patent No.: US 7,033,389 B2
(45) Date of Patent: Apr. 25, 2006

(54) TUBULAR PROSTHESIS FOR EXTERNAL AGENT DELIVERY

(75) Inventor: John E. Sherry, Needham, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 368 days.

(21) Appl. No.: 09/978,988

(22) Filed: Oct. 16, 2001

(65) Prior Publication Data

US 2003/0074048 A1    Apr. 17, 2003

(51) Int. Cl.
*A61F 2/06* (2006.01)

(52) U.S. Cl. .................................. 623/1.42; 623/1.13

(58) Field of Classification Search ............... 623/1.13, 623/1.42–1.48
See application file for complete search history.

(56) References Cited

U.S. PATENT DOCUMENTS

| | | |
|---|---|---|
| 3,657,744 A | 4/1972 | Ersek |
| 4,300,244 A | 11/1981 | Bokros |
| 4,409,172 A | 10/1983 | Ward, Jr. et al. |
| 4,732,152 A | 3/1988 | Wallsten et al. |
| 4,969,458 A | 11/1990 | Wiktor |
| 5,049,132 A * | 9/1991 | Shaffer et al. ......... 604/101.02 |
| 5,078,726 A | 1/1992 | Kreamer |
| 5,123,917 A | 6/1992 | Lee |
| 5,156,620 A * | 10/1992 | Pigott ....................... 623/1.25 |
| 5,282,824 A | 2/1994 | Gianturco |
| 5,330,500 A | 7/1994 | Song |
| 5,366,504 A | 11/1994 | Anderson et al. |
| 5,383,926 A | 1/1995 | Lock et al. |
| 5,387,235 A | 2/1995 | Chuter |
| 5,389,106 A | 2/1995 | Tower |
| 5,456,713 A | 10/1995 | Chuter |
| 5,507,769 A | 4/1996 | Marin |
| 5,507,771 A | 4/1996 | Gianturco |
| 5,522,881 A | 6/1996 | Lentz |
| 5,545,135 A * | 8/1996 | Iacob et al. ............... 604/103.1 |
| 5,558,642 A * | 9/1996 | Schweich et al. ...... 604/103.01 |
| 5,562,726 A | 10/1996 | Chuter |
| 5,562,727 A * | 10/1996 | Turk et al. ................. 623/1.44 |
| 5,607,468 A * | 3/1997 | Rogers et al. ............... 128/898 |

(Continued)

FOREIGN PATENT DOCUMENTS

DE      3902364       8/1989

(Continued)

OTHER PUBLICATIONS

Copy of Search Report issued on Jan. 20, 2003 for International Application No. PCT/US 02/30695.

(Continued)

*Primary Examiner*—(Jackie) Tan-Uyen T. Ho
(74) *Attorney, Agent, or Firm*—Hoffmann & Baron, LLP

(57) ABSTRACT

A tubular prosthesis, which may be an endovascular prosthesis, is provided which includes a tubular member (stent or stent/graft combination) and an outer covering having portions sealed to the tubular member. The tubular member is impervious to a pre-determined fluid, particularly an occluding fluid, while the outer cover is pervious to the pre-determined fluid. In one aspect of the present invention, the implantation of the prosthesis allows for occluding fluid to weep from the prosthesis and into a sac of an aneurysm to cause occlusion thereof without introducing the occluding fluid into the blood stream. In this manner, a Type II failure of the prosthesis may be avoided. In other aspects of the invention, therapeutic agents may be delivered and/or a seal may be formed about the prosthesis to prevent a Type I failure.

31 Claims, 3 Drawing Sheets

U.S. PATENT DOCUMENTS

| | | | |
|---|---|---|---|
| 5,618,299 A | | 4/1997 | Khosravi et al. |
| 5,628,784 A | * | 5/1997 | Strecker .................... 623/1.11 |
| 5,665,117 A | | 9/1997 | Rhodes |
| 5,685,847 A | * | 11/1997 | Barry ...................... 604/96.01 |
| 5,693,088 A | * | 12/1997 | Lazarus .................... 623/1.35 |
| 5,697,968 A | * | 12/1997 | Rogers et al. ............. 623/1.24 |
| 5,735,892 A | | 4/1998 | Myers et al. |
| 5,785,679 A | * | 7/1998 | Abolfathi et al. ........... 604/509 |
| 5,797,951 A | | 8/1998 | Mueller |
| 5,824,038 A | | 10/1998 | Wall |
| 5,824,054 A | | 10/1998 | Khosravi et al. |
| 5,843,033 A | * | 12/1998 | Ropiak ................. 604/103.01 |
| 5,843,166 A | | 12/1998 | Lentz et al. |
| 5,951,599 A | | 9/1999 | McCrory |
| 5,961,545 A | | 10/1999 | Lentz et al. |
| 6,010,529 A | | 1/2000 | Herweck et al. |
| 6,096,070 A | | 8/2000 | Ragheb et al. |
| 6,149,641 A | * | 11/2000 | Ungs .......................... 604/501 |
| 6,193,746 B1 | * | 2/2001 | Strecker .................... 623/1.13 |
| 6,270,523 B1 | | 8/2001 | Herweck et al. |
| 6,309,343 B1 | | 10/2001 | Lentz et al. |
| 6,379,379 B1 | * | 4/2002 | Wang ........................ 623/1.15 |
| 6,379,382 B1 | * | 4/2002 | Yang ........................ 623/1.42 |
| 6,395,019 B1 | * | 5/2002 | Chobotov .................. 623/1.13 |
| 6,613,084 B1 | * | 9/2003 | Yang ........................ 623/1.42 |
| 6,656,214 B1 | * | 12/2003 | Fogarty et al. ............. 623/1.13 |
| 2001/0027338 A1 | | 10/2001 | Greenberg |

FOREIGN PATENT DOCUMENTS

| | | |
|---|---|---|
| EP | 0 657 147 | 6/1995 |
| EP | 0 689 805 | 1/1996 |
| EP | 0 737 453 | 10/1996 |
| SU | 1457 921 | 2/1989 |
| WO | WO 95/02377 | 1/1995 |
| WO | WO 95/05132 | 2/1995 |
| WO | WO 95/29647 | 11/1995 |
| WO | WO 96/00103 | 1/1996 |
| WO | WO 96/10967 | 4/1996 |
| WO | WO 96/22745 | 8/1996 |
| WO | WO 96/28115 | 9/1996 |
| WO | WO 96/33672 | 10/1996 |
| WO | WO 96/35577 | 11/1996 |
| WO | WO 9811847 A | 3/1998 |

OTHER PUBLICATIONS

Lawrence, Jr. D.D., Charnsangavej, C., Wright, K.C., Gianturco, C., and Wallace, S., Percutaneous Endovascular Graft: Experimental Evaluation. Radiology 1986; 163:357-360.

* cited by examiner

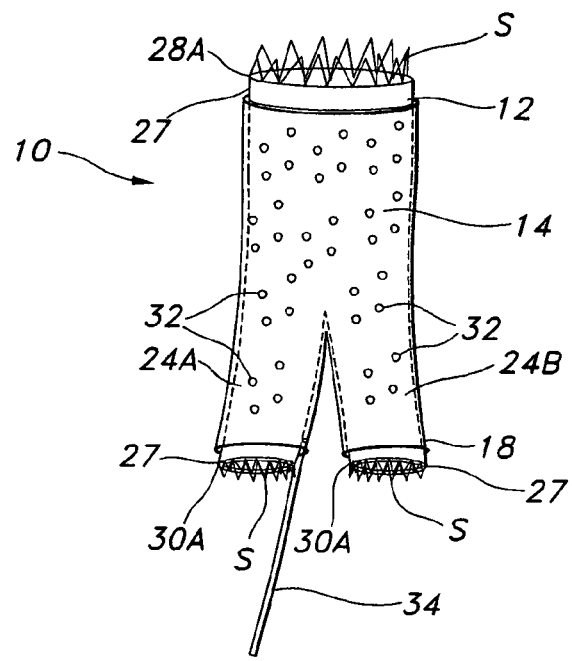
FIG. 4
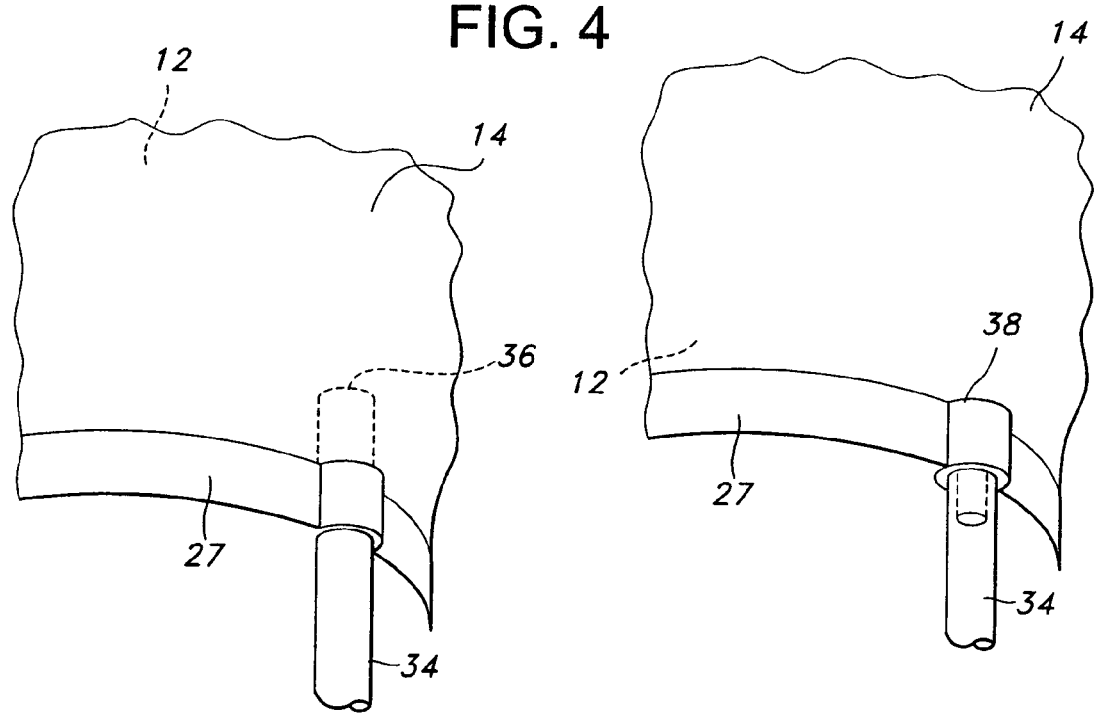
FIG. 6A
FIG. 6B

TUBULAR PROSTHESIS FOR EXTERNAL AGENT DELIVERY

FIELD OF THE INVENTION

This invention relates to tubular prostheses, including, but not limited to, endovascular grafts and stent/grafts, for maintaining patency of blood vessels and treating aortic artery aneurysms, and tubular conduits for maintaining patency in other bodily passageways.

BACKGROUND OF THE PRIOR ART

It is known in the prior art to use endovascular prostheses to treat aortic artery aneurysms ("AAA"). Such treatment includes implanting a stent, or stent/graft, within the diseased vessel to by-pass the anomaly. An aneurysm is a sac formed by the dilation of the wall of the artery, which may be congenital, but usually is caused by disease and, occasionally, by trauma. With reference to FIG. 1, sac 1 of aneurysm A is defined by dilated portions 2 of aortic artery AA. With the collection of blood and other embolic material in the sac 1, and being subjected to hemodynamic pressure, the aneurysm A may rupture, if untreated, causing internal bleeding.

Techniques had been developed in the prior art where diseased portions of a blood vessel, such as with an aneurysm, were ablated and replaced with a prosthetic member, such as that shown in U.S. Pat. No. 4,938,740 to Melbin. This technique, however, required open surgery. As an improvement over this technique, endovascular emplacement techniques have been developed to implant grafts and stent/grafts into a vessel from a remote puncture site, thereby obviating the need for open surgery. For example, as shown in FIG. 1, an endovascular prosthesis 3 (stent or stent/graft) is positioned to by-pass the aneurysm A with ends 4, 5 of the prosthesis being in contiguous contact with healthy portions of the aortic artery AA, the prosthesis 3 having been introduced endovascularly (e.g. with a catheter). Accordingly, if the aneurysm A was to rupture, blood flow through the aortic artery AA would be uninterrupted, and internal bleeding generally avoided.

Although considerable success has been enjoyed with stent and stent/graft performance, failures have been noted and predominantly classified in four classes: Types I–IV. Type I failures relate to leaks (referred to as endoleaks) between the vascular prosthesis and the vessel wall. For example, with reference to FIG. 1, a Type I failure would be blood weeping about the end 4 of the prosthesis 3 into the sac 1.

A Type II failure involves blood flowing into the aneurysm sac through collateral arteries. Again, with reference to FIG. 1, the sac 1 may be in fluid communication with blood vessels BV, other than the aortic artery AA. Typically, lumbar arteries are in fluid communication (directly or indirectly) with an aneurysm sac. Because blood flow out of the sac 1 is prevented, hemodynamic pressure away from the sac 1 is not present. However, because of hemodynamic pressure within blood vessels in communication with the sac 1, blood flow, nevertheless, is directed into the sac 1 (as shown by arrows). A technique has been developed in the prior art which calls for embolizing the blood vessels BV, such as with embolus coils, thereby isolating the sac 1 from collateral blood flow. However, an additional procedure would be required for embolization.

A Type III failure is a mechanical failure, wherein a hole may be ripped into the prosthesis (e.g., excessive wear at a metal/non-metal (fabric or polymer) interface) or poor integrity exists at a connection, or connections, between modular components of a prosthesis, (e.g., extensions may be connected to the prosthesis to obtain improved securement in one or both of the iliac arteries.) For example, as shown in FIG. 1, a hole 6 may be torn into the prosthesis 2, or poor sealing is obtained at the connection between the prosthesis 3 and an extension 7.

A Type IV failure relates to excessive prosthesis porosity, wherein blood seeps through the prosthesis regardless of the integrity of sealing and mechanical connections.

As can be readily appreciated, even with the successful implantation of an endovascular prosthesis, failures may occur thereafter. It has been found that Type II failures are most prevalent, and may effect up to 30% of all implanted prostheses. Accordingly, there is a clear need for an endovascular prosthesis which can reduce the likelihood, and ideally eliminate, Type II failures.

SUMMARY OF THE INVENTION

To overcome deficiencies in the prior art, a tubular prosthesis is provided that includes a tubular member, which is impervious to a pre-determined fluid, and an outer covering, which is pervious to the pre-determined fluid. Accordingly, in one aspect of the invention, the prosthesis may be an endovascular prosthesis, and a fluid, which is effective for occluding the sac of an aneurysm, may be introduced by the prosthesis into a space between the tubular member and the outer covering. The fluid will transmit through the outer covering and weep into the sac to cause at least partial occlusion thereof without the occluding fluid being introduced into the blood stream. In this manner, collateral blood flow may be prevented from flowing into the aneurysm sac and collecting therein.

A fluid conduit, preferably a microcatheter, is connected to the endovascular prosthesis so as to be in fluid communication with the space defined between the tubular member and the outer covering. It is preferred that the fluid conduit be connected to the prosthesis prior to introduction into the body, with such connection continuing through deployment of the prosthesis and engagement with the vessel. Prior to withdrawal of the deployment device used to implant the prosthesis (e.g. an introducer catheter), occluding fluid is injected through the fluid conduit and between the tubular member and the outer cover with an effective amount of fluid being introduced to achieve at least partial occlusion of the aneurysm sac. With the outer cover being pervious to the fluid, the fluid transmits therethrough. Upon the effective dose having been injected into the space, the fluid conduit is caused to detach from the prosthesis, and withdrawn with any deployment device, such as a guidewire.

The tubular member may be of any endovascular prosthetic construction known in the prior art, including graft and stent/graft configurations (including single layer and multi-layer grafts and stent/grafts). The tubular member may be a textile graft, a polymeric graft, or a combination thereof. In addition, the tubular member may have a stent reinforcement (single stent or multiple stents), such stent being self-expanding or expandable by a distensible member, such as a balloon.

The outer covering may be formed of a textile, a polymeric film, or a combination thereof. In addition, the outer covering may be made pervious to the occluding fluid through inherent porosity of the constituent material of the outer covering (e.g., porosity of expanded polytetrafluoroethylene (ePTFE)), and/or, more preferably, through cut apertures physically defined in the outer covering. To attempt to achieve even distribution of the occluding fluid, it is desired to make the outer covering increasingly pervious to the fluid at locations further from the fluid conduit.

The occluding fluid is preferably a liquid embolic, which may be an alginate, an hyaluronic acid, and/or a cyanoacrylate, or an admixture thereof. Alternatively, a sclerosing agent may be used, as well as cross-linking polymers (polyurethanes, silicones), thrombin, and autologous clot(s). The occluding fluid may be in a liquid state or a gel, and may be formed with solids in a suspension of either state (liquid or gel).

In another aspect of the invention, therapeutic agents, with or without the occluding fluid, may be transmitted via the subject invention.

The tubular prosthesis may be used as an endovascular prosthesis, as well as, in other applications to maintain patency of a bodily passageway, such as the esophagus, trachea, colon, biliary tract, urinary tract, prostate, and brain.

These and other features of the invention would be better understood through a study of the following detailed description and accompanying drawings.

BRIEF DESCRIPTION OF DRAWINGS

FIG. 4 shows a second embodiment of a tubular prosthesis of the subject invention;

FIGS. 6A and 6B are schematics depicting the connections of a fluid conduit to the prosthesis.

DETAILED DESCRIPTION OF THE INVENTION

Figure 2:
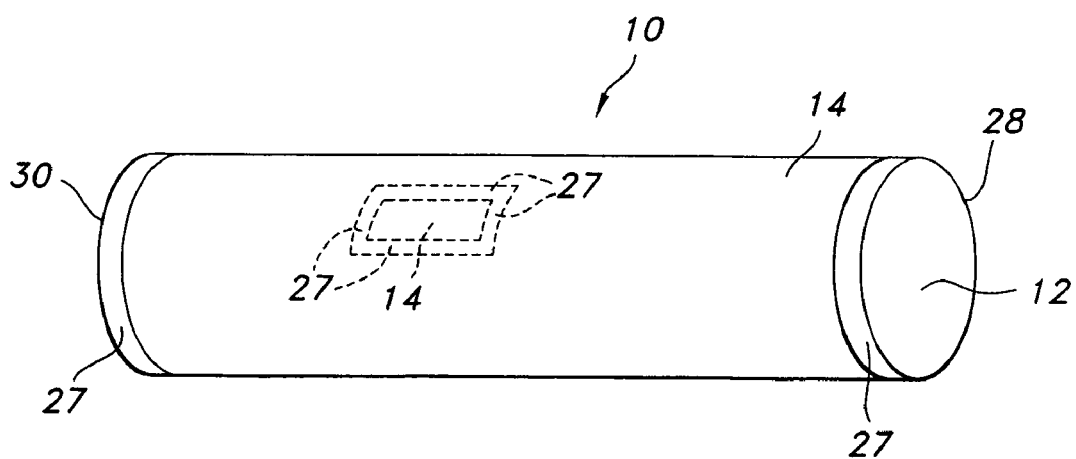
FIG. 2 shows a first embodiment of a tubular prosthesis of the subject invention.

With reference to FIGS. 2 and 4, first and second embodiments of a prosthesis 10 are respectively depicted therein. Reference will be made herein to the prosthesis being endovascular, although as pointed out above, the prosthesis may be used in other applications. In each embodiment, the endovascular prosthesis 10 includes a tubular member 12, 12a and an outer covering 14. The tubular member 12, 12a is impervious to the transmission therethrough of a pre-determined fluid, particularly an occluding fluid, while the outer covering 14 is pervious to the transmission therethrough of the pre-determined fluid. Accordingly, the prosthesis 10 can be utilized to at least partially occlude the sac of an aneurysm, as described below. The endovascular prosthesis 10 may take any shape or form as required, although commonly, the prosthesis 10 will have a cylindrical shape (as shown in FIG. 2), or a bifurcated Y-shape (as shown in FIG. 4). Although only these two shapes are shown, other shapes are possible.

Figure 3:
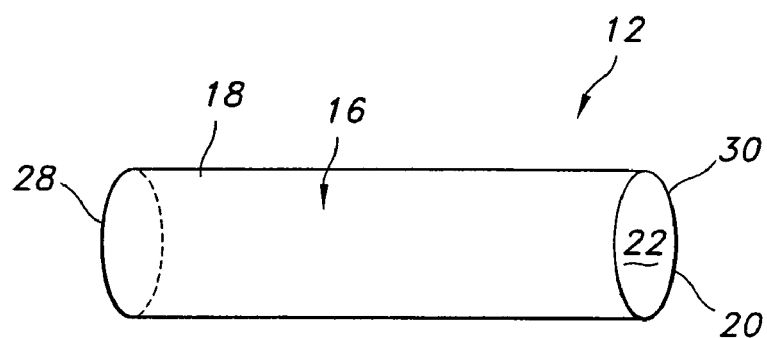
FIG. 3 shows a tubular member for use with the first embodiment of the subject invention.
Figure 5:
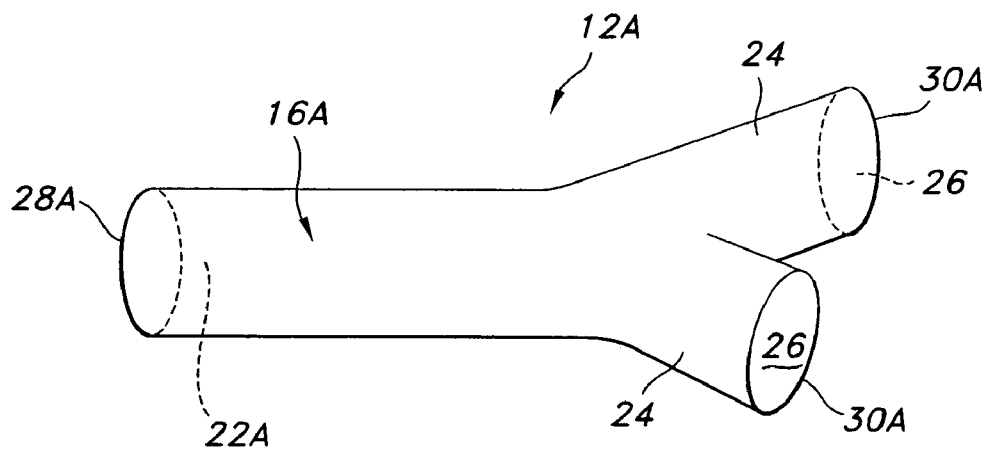
FIG. 5 shows a bifurcated Y-shaped tubular member for use with the second embodiment of the subject invention.

The tubular member 12, 12a may be of any endovascular prosthetic construction known in the prior art, including graft and stent/graft configurations. With reference to FIG. 3, in the first embodiment, the tubular member 12 has a cylindrical shape with a tubular wall 16 having an outer surface 18 and an inner surface 20 defining a single lumen 22. The tubular member 12 need not be formed as a right cylinder, and may be irregularly formed (e.g. bent; eccentric). In a second embodiment, as shown in FIG. 5, the tubular member 12a has a bifurcated Y-shape with a first tubular portion 16a, defining a lumen 22a, from which extend branches 24a, 24b, each defining a lumen 26 in fluid communication with the lumen 22a. As is readily apparent, the tubular member 12, 12a defines the general shape of the endovascular prosthesis 10, and thus, the tubular member 12, 12a is formed to any desired shape of the endovascular prosthesis 10.

Figure 1:
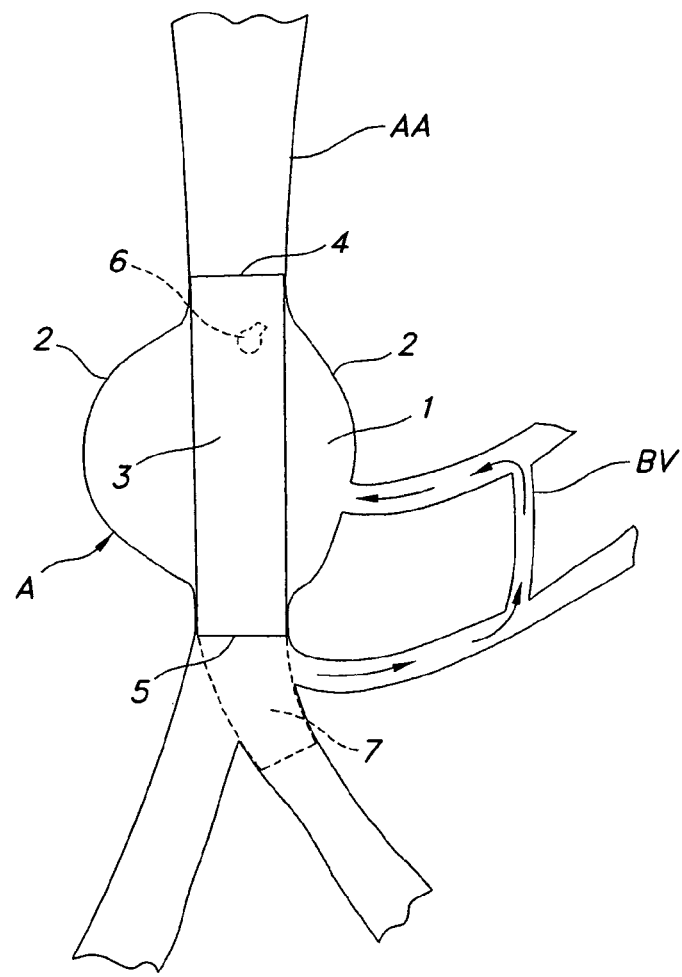
FIG. 1 is a schematic of an aortic artery aneurysm with an endovascular prosthesis bypassing thereby.

The tubular member 12, 12a may be a textile graft, a polymeric graft, or a combination thereof (including single layer and multi-layer configurations). In addition, the tubular member 12, 12a may have a stent reinforcement, such stent being self-expanding or expandable by a distensible member, such as a balloon (stents S are shown in FIG. 5) (a single stent or multiple stents may be used). Graft and stent/graft designs are well known in the art, and any design compatible with the invention may be used. The tubular member 12, 12a is shown in each embodiment as a unitary member, regardless of shape. As an alternative, the tubular member 12, 12a may be formed from modular components and/or have the shape as shown, but connected to extensions as known in the prior art (e.g. the extension 7 shown in FIG. 1).

The outer covering 14 is disposed on, and preferably sealed to, portions of the outer surface of the tubular member 12, 12a. In a preferred embodiment, as shown in FIGS. 2 and 4, the outer covering 14 is generally coextensive with the tubular member 12, 12a. The outer covering 27 is sealed to the tubular member 14 using any technique known to those skilled in the art, including, but not limited to, fusing and bonding. Sealed portions 27 of the outer covering 14 are preferably spaced-apart so that unsealed portions of the outer covering 14 are bounded by the sealed portions 27. In this manner, entrapped space between the tubular member 12, 12a and the outer covering 14 which is at least partially bounded by the sealed portions 27 of the outer covering 14 defines a pocket 15 for receiving occluding fluid. Optionally, the outer covering 14 can be sealed at multiple locations to define multiple pockets 15. Because of the impervious nature of the tubular member 12, 12a and the sealed portions 27, the fluid can only escape from the pocket 15 via transmission through the outer covering 14. As shown in FIG. 2, it is preferred to seal the outer covering 14 at portions in proximity to the ends 28 and 30 of the tubular member 12. With respect to the tubular member 12a, as shown in FIG. 4, it is preferred that the outer covering 14 have sealed portions 27 in proximity to all ends 28a and 30a. Accordingly, the pocket 15 is generally coextensive with the tubular member 12, 12a.

As a variation, the outer covering 14 may be formed as a patch which covers only a portion of the tubular member 12, 12a, as shown in dashed lines in FIG. 2. Although not shown, the outer covering 14 may form an annular band about the tubular member 12, 12a. Furthermore, multiple outer coverings 14 may be used as patches to form a discontinuous or regular pattern.

The outer covering 14 may be formed of a textile, a polymeric film, or a combination thereof. The critical aspect of the outer covering 14 is for it to be pervious to the occluding fluid. The outer covering 14 may be made pervious through inherent porosity of the constituent material of the outer covering, for example due to the porosity of expanded polytetrafluoroethylene (ePTFE). In addition, in a preferred manner of achieving the pervious nature of the outer covering 14, cut apertures 32 may be physically defined in the outer covering 14, as shown in FIG. 4. It is also possible to combine these two approaches.

In a preferred embodiment, a fluid conduit 34, preferably a microcatheter, is connected to the endovascular prosthesis 10 so as to convey the occluding fluid thereto. With reference to FIGS. 6a and 6b, the fluid conduit 34 may be in direct fluid communication with the pocket 15, with an end 36 of the fluid conduit 34 being located therein. As can be appreciated, to achieve this result, the fluid conduit 34 must breach the sealed portions 27. This can be readily done during manufacturing by causing the sealed portions 27 to be formed about the fluid conduit 34. However, upon removal of the fluid conduit 34, an open passage will be defined through the sealed portions 27. Thus, it is preferred to only use the technique where inherent viscosity of the occluding fluid will prevent leakage of the occluding fluid through the open passage.

As a preferred alternative, a valve 38 (preferably one-way) is disposed in communication with the pocket 15, so that the fluid conduit 34 is in indirect communication with the pocket 15 via the valve 38. The construction of the valve 38 and the fluid conduit 34 may be the same as that used with silicone balloon distension, (e.g., the system sold under the trademark "APOLLO" by Target Therapeutics of Fremont, Calif.).

In a preferred embodiment, the fluid conduit 34 is connected to the endovascular prosthesis 10 prior to insertion into the human body. After deployment of the endovascular prosthesis 10, using any technique and device known, the fluid conduit 34 preferably remains connected to the prosthesis 10. It is envisioned that a Strecker pull-string type deployment device or a pull-back sheath deployment device would operate well with the subject invention. An effective amount of occluding fluid is conveyed through the fluid conduit 34 into the pocket 15 to at least partially occlude the sac of the aneurysm being treated. With the effective dose having been conveyed, the fluid conduit 34 is caused to be detached, preferably with a sufficiently strong pull of the fluid conduit 34. With the aforementioned prior art silicone balloon distension systems, minimum threshold forces have been developed to achieve such detachment and it is contemplated herein to use similar methodology to require minimum threshold forces for detachment. Once detached, the fluid conduit 34 is removed with any other deployment devices, such as an introducer catheter.

The occluding fluid is preferably a liquid embolic, which may be an alginate, an hyaluronic acid, and/or a cyanoacrylate, or an admixture thereof. Alternatively, a sclerosing agent may be used, as well as cross-linking polymers (polyurethanes, silicones), thrombin, and autologous clot(s). The occluding fluid may be in a liquid state or a gel, and may be formed with solids in a suspension of either state (liquid or gel).

With the occluding fluid being disposed within the pocket 15, the fluid may transmit through the outer covering 14 to at least partially occlude the sac of the aneurysm being treated without the fluid being introduced into the blood stream.

In another aspect of the invention, therapeutic agents, with or without the occluding fluid, may be transmitted via the subject invention in the same manner described with respect to the occluding fluid, including: anti-thrombogenic agents (such as heparin, heparin derivatives, urokinase, and PPack (dextrophenylalanine proline arginine chloromethylketone); antiproliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

In a further aspect of the subject invention, the occluding fluid may be introduced via the endovascular prosthesis 10 between the blood vessel wall and the endovascular prosthesis 10 so as to at least partially seal against endoleaks about the prosthesis 10 (i.e., Type I failure). (With other applications of the subject invention, the occluding fluid is disposed between the wall of the bodily passageway and the prostheis 10.) The occluding fluid may create a blood-vessel seal (in whole or in part) with or without occluding the sac of the aneurysm. Preferably, a ring-shaped pocket 15 may be provided in proximity to an end of endovascular prosthesis 10 through which the occluding fluid may be delivered to form the seal; as such, an annular seal may be desirably defined about the prosthesis 10 in proximity to an end so as to restrict endoleaks. The ability to seal against endoleaks is particularly desirable where a blood vessel has an irregularly formed blood vessel.

In a further enhancement of the invention, it is preferred that the outer covering 14 be increasingly pervious to the occluding fluid and/or therapeutic agents at further distances from the fluid conduit 34. For example, with reference to FIG. 4, the cut apertures 32 are formed increasingly larger further from the fluid conduit 35 (i.e., as approaching the end 28A) and/or an increasingly greater number of cut apertures 32 is provided further from the fluid conduit 34 (i.e., the density of cut apertures 32 increases with distance from the fluid conduit 34) to provide less resistance to the distribution of the occluding fluid and/or therapeutics being conveyed via the fluid conduit 34. Likewise, the cut apertures 32 are formed increasingly larger and/or greater in number as located further down the branch portion 24b, to which the fluid conduit 34 is not attached. As an alternative, or as an additional option, the porosity of the constituent material may be gradually increased at further locations from the source of the occluding fluid and/or therapeutic agents to also provide less fluid resistance.

Various changes and modifications can be made to the present invention. It is intended that all such changes and modifications come within the scope of the invention as set forth in the following claims.

What is claimed is:

1. A tubular prosthesis comprising:
    a prosthetic tubular member having a wall with an inner surface and an outer surface, said wall being impervious to transmission therethrough of a pre-determined fluid;
    an outer covering having portions sealed to said outer surface of said tubular member, said outer cover being pervious to transmission therethrough of said pre-determined fluid; and
    a fluid conduit having an end communicating with space defined between said tubular member and said outer covering, said fluid conduit formed to convey said pre-determined fluid to said space, wherein said outer covering is increasingly pervious to transmission therethrough of said predetermined fluid at locations increasingly further from said end of said fluid conduit.

2. A prosthesis as in claim 1, wherein said tubular member is formed of a polymeric material.

3. A prosthesis as in claim 1, wherein said tubular member is formed of a textile material.

4. A prosthesis as in claim 1, wherein said tubular member includes a polymeric material and a textile material.

5. A prosthesis as in claim 1, wherein said outer covering is generally coextensive with said tubular member.

6. A prosthesis as in claim 1, wherein said tubular member has a first opening, said outer covering being sealed to said tubular member in proximity to said first opening.

7. A prosthesis as in claim 1, wherein said tubular member is cylindrical.

8. A prosthesis as in claim 1, wherein said tubular member is generally Y-shaped with a single lumen being in fluid communication with two minor lumens.

9. A prosthesis as in claim 1, wherein said outer covering is a porous material.

10. A prosthesis as in claim 1, wherein cut apertures are formed in said outer covering.

11. A prosthesis as in claim 10, wherein said cut apertures are each generally equal in size.

12. A prosthesis as in claim 10, wherein said cut apertures are of various sizes.

13. A prosthesis as in claim 10, wherein said cut apertures are unevenly dispersed.

14. A prosthesis as in claim 1, wherein said end of said fluid conduit directly communicates with said space with said end being located in said space.

15. A prosthesis as in claim 1, wherein said end indirectly communicates with said space via a valve.

16. A prosthesis as in claim 1, wherein cut apertures are formed in said outer covering, said cut apertures being increasingly larger as located increasingly further located from said end of said fluid conduit.

17. A prosthesis as in claim 1, wherein cut apertures are formed in said outer covering, the density of said cut apertures increasing with distance from said end of said fluid conduit.

18. A prosthesis as in claim 1, wherein said outer covering is increasingly porous at locations increasingly further from said end of said fluid conduit.

19. A prosthesis as in claim 1, wherein said pre-determined fluid is an occluding fluid.

20. A prosthesis as in claim 19, wherein said occluding fluid is an embolic liquid selected from the group consisting of alginates, hyaluronic acid, cyanoacrylates, and admixtures thereof.

21. A prosthesis as in claim 19, wherein said occluding fluid is selected from the group consisting of sclerosing agents, polyurethanes, silicones, and admixtures thereof.

22. A prosthesis as in claim 19, wherein said occluding fluid includes thrombin.

23. A prosthesis as in claim 19, wherein said occluding fluid includes an autologous clot.

24. A prosthesis as in claim 1, wherein said tubular member is a graft.

25. A prosthesis as in claim 1, wherein said tubular member is a stent/graft combination.

26. A prosthesis as in claim 25, wherein said stent is expandable.

27. A prosthesis as in claim 26, wherein said stent is self-expanding.

28. A prosthesis as in claim 1, wherein said sealed portions of said outer covering at least partially bound a pocket for receiving said pre-determined fluid.

29. A prosthesis as in claim 28, wherein said pocket is generally coextensive with said tubular member.

30. A prosthesis as in claim 1, wherein said pre-determined fluid is a therapeutic agent.

31. A prosthesis as in claim 1, wherein the prosthesis is an endovascular prosthesis.

* * * * *